(12) United States Patent
Kammermeier et al.

(10) Patent No.: US 6,417,371 B1
(45) Date of Patent: Jul. 9, 2002

(54) PROCESS FOR PREPARING 6-(4-CHLOROPHENYL)-2,2-DIMETHYL-7-PHENYL-2,3-DIHYDRO-1H-PYRROLIZIN-5-YL-ACETIC ACID

(75) Inventors: Thomas Kammermeier, Ulm; Stefan Laufer, Blaubeuren; Philipp Merckle, Blaubeuren-Weiler; Hans-Guenter Striegel, Blaustein, all of (DE)

(73) Assignee: Merckle GmbH, Ulm (DE)

( * ) Notice: Subject to any disclaimer, the term of this patent is extended or adjusted under 35 U.S.C. 154(b) by 0 days.

(21) Appl. No.: 09/769,742

(22) Filed: Jan. 26, 2001

(30) Foreign Application Priority Data

Jan. 28, 2000 (MX) .............................................. 001047

(51) Int. Cl.[7] ........................ C07D 209/52; A61K 31/40
(52) U.S. Cl. ........................ 548/516; 548/571; 548/577; 514/413; 514/427
(58) Field of Search ................................ 548/516, 571, 548/577; 514/413, 427

(56) References Cited

U.S. PATENT DOCUMENTS 5,260,451 A   11/1993   Dannhardt et al.
5,939,415 A    8/1999   Laufer et al.

(List continued on next page.)

FOREIGN PATENT DOCUMENTS

WO   WO 95/32970 A1   12/1995
WO   WO 95/32971 A1   12/1995
WO   WO 95/32972 A1   12/1995

OTHER PUBLICATIONS

Rabasseda, X. et al., "ML–3000, Antiinflammatory Cyclooxygenase and 5–Lipoxygenase Inhibitor", *Drugs of the Future*, 1995, pp. 1007–1009, v. 20(10), Prous Science Publishers, Spain.

(List continued on next page.)

*Primary Examiner*—Floyd D. Higel
*Assistant Examiner*—Golan M. M. Shameem
(74) *Attorney, Agent, or Firm*—Rothwell, Figg, Ernst & Manbeck

(57) ABSTRACT

The present invention relates to a process process for the preparation of the compound of the formula I

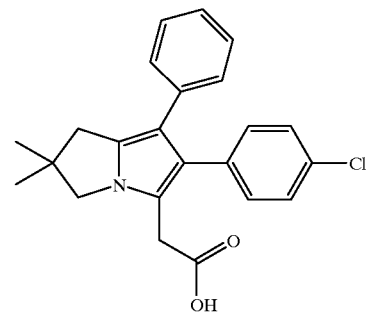

where the compound of the formula III

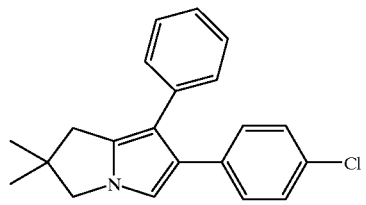

is reacted with oxalyl chloride and the product obtained is treated with hydrazine and an alkali metal hydroxide in the aqueous phase at elevated temperature, after treatment is complete a three-phase system is produced by addition of an ether and the compound of the formula I is obtained by acidifying the middle phase.

The invention moreover relates to a polymorph of the compound of the formula I.

18 Claims, 9 Drawing Sheets

U.S. PATENT DOCUMENTS 5,942,535 A     8/1999    Laufer et al.
5,958,943 A     9/1999    Laufer et al.

OTHER PUBLICATIONS

Laufer, S. et al, "Synthesis and Evaluation of a Novel Series of Pyrrolizine Derivatives as Dual Cyclooxygenase–1 and 5–Lipoxygenase Inhibitors", *Arch. Pharm. Pharm. Med. Chem.*, 1997, pp. 307–312, v. 330, Wiley–VCH Verlag GmbH, Germany.

Laufer, S. et al. "(6,7–Diaryldihydropyrrolizin–5–yl)acetic Acids, a Novel Class of Potent Dual Inhibitors of Both Cyclooxygenase and 5–Lipoxygenase", *J. Med. Chem.*, 1994, pp. 1894–1897, v. 37, American Chemical Society.

Cossy et al (1997): J. Org. Chem. vol. 62, 7900–7901.*

Cossy et al (1999): Tetrahedron. vol. 55, 5145–5156.*

* cited by examiner

PROCESS FOR PREPARING 6-(4-CHLOROPHENYL)-2,2-DIMETHYL-7-PHENYL-2,3-DIHYDRO-1H-PYRROLIZIN-5-YL-ACETIC ACID

DESCRIPTION OF THE INVENTION

The present invention relates to a process for the preparation of 6-(4-chlorophenyl)-2,2-dimethyl-7-phenyl-2,3-dihydro-1H-pyrrolizin-5-ylacetic acid (ML 3000) and to a novel polymorph of ML 3000 which is designated as polymorph A.

ML 3000 is a promising inhibitor of cyclooxygenase and 5-lipoxygenase and is thus suitable for the treatment of disorders of the rheumatic type and for the preventive treatment of allergically induced disorders, for this see, for example, Drugs of the Future 1995, 20 (10):1007–1009. A possible route for preparation is also found in this publication. Further preparation possibilities are described in EP-A-397175, WO95/32970, WO95132971, WO95/32972, Archiv der Pharmazie 312, 896–907 (1979); and 321, 159–162 (1988), J. Med. Chem. 1994 (37), 1894–1897, Arch. Pharm. Pharm. Med. Chem. 330, 307–312 (1997). In all these syntheses, the construction of the pyrrolizine parent structure is carried out according to the method shown in the reaction scheme:

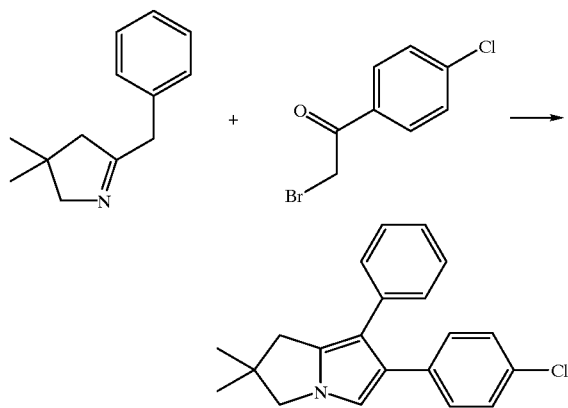

The reaction is carried out in methylene chloride, ethanol or diethyl ether. The hydrogen bromide formed in the reaction is trapped by addition of aqueous sodium bicarbonate solution.

The introduction of the acetic acid radical into position 5 is then carried out by reaction with ethyl diazoacetate or ethyl oxalyl chloride and subsequent hydrolysis or hydrolysis and reduction of the keto group with hydrazine.

Arch. Pharm. 312, 896–907 (1979) describes the following reaction:

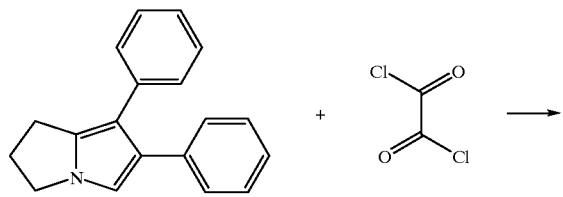

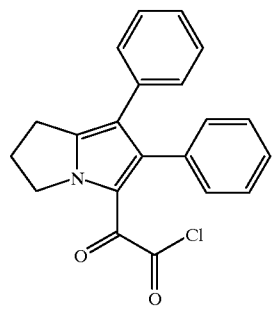

The reaction is carried out in benzene as a solvent. The COCOCl group, is then not converted into the acetic acid group, however, but reacted with diethylamine.

WO95/32970, WO95/32971 and WO95/32972 describe the introduction of the acetic acid radical into compounds which are structurally related to ML-3000 by reaction of these pyrrolizine compounds with oxalyl chloride or ethyl oxalyl chloride and subsequent reduction with hydrazine and potassium hydroxide (Huang Minlon variant of the Wolff-Kishner reduction). More detailed information on the experimental procedure is found only in Example 5C of WO95/32971. The reaction of the pyrrolizine compound with oxalyl chloride is then carried out in THF. Water and hydrazine hydrate are added to the reaction product and, the tetrahydrofuran is distilled off, the residue is treated with diethylene glycol and with potassium hydroxide and heated to 140° C. with simultaneous removal of the water. The reaction mixture is subsequently treated with water, acidified and the precipitated carboxylic acid is taken up in diethyl ether. The product is purified by stirring the ethereal solution for some time over a drying agent, such as anhydrous sodium sulfate or magnesium sulfate, and allowing it to stand, then filtering off the water-saturated sulfate and finally evaporating the ether in the presence of heat. The substance crystallizing from the mother liquor on concentration is collected and dried.

For the industrial preparation of ML 3000, the introduction of the acetic acid radical using oxalyl chloride is preferred. However, it has been shown that after the above reaction in the previous process for the isolation and purification of the crude material the yield decreases severely and a number of decomposition products are newly formed in the purification step and additionally during the drying, so that a further laborious purification of the ML 3000, e.g. by recrystallization, is necessary in order to obtain pharmaceutical quality.

In the preparation process already mentioned, compounds structurally analogous to ML 3000 were purified and crystallized by the following methods.

In J. Med. Chem. 1994, 37, 1894–1897, the ethanolic/alkaline solution of the sodium salt of ML 3000 obtained from the hydrolysis of the ethyl ester is acidified with phosphoric acid and extracted with a mixture of 3 parts of diethyl ether and 1 part of methylene chloride. The solid which remains after drying over sodium sulfate and after stripping off the solvent mixture is resuspended using diisopropyl ether, filtered off and dried. For the preparation of ML 3000, reference is made to Arch. Pharm. 321, 159–162 (1988) (for discussion see below).

In Arch. Pharm. Pharm. Med. Chem. 330, 307–312 (1997), heterocyclic structural analogs of ML 3000 which are formed from 2-oxoacetic acid precursors according to the Huang-Minlon method are obtained by concentrating the eluates obtained from a short silica gel column using diethyl ether.

In Arch. Pharm. 321, 159–162 (1988), the ethyl esters of some acids structurally related to ML 3000 are hydrolyzed in ethanol KOH, after the hydrolysis the acids are liberated from the aqueous/ethanolic mother liquor of the potassium salts by means of 6% strength phosphoric acid and taken up in diethyl ether. After volume reduction, the acids are adsorbed therefrom on neutral alumina. After ether elution of the neutral impurities, the carboxylic acids are desorbed from the mineral support by the action of aqueous sodium dihydrogenphosphate solution and in turn taken up in diethyl ether. This second diethyl ether extract is concentrated until it crystallizes, the crystals are separated off and, after addition of pentane to precipitate a second crystal fraction, the volume of the ethereal mother liquor is again reduced.

In the thesis of Kiefer (Frankfurt, 1992), for the preparation of an analogous pyrrolizin-5-yl-acetic acid the corresponding 2-oxoacetic acid is subjected to the Huang-Minlon reduction method. Before the liberation of the pyrrolizin-5-ylacetic acid contained in the reaction mixture as a potassium salt, the neutral to alkaline impurities and contaminants are removed by a preliminary extraction of the aqueous/alkaline product phase with ethyl acetate. Only then is the carboxylic acid precipitated by means of 6N HCl and taken up in diethyl ether. The diethyl ether extracts are washed with water, dried and the solvent is completely removed until a crystalline solid is present, which is then washed with cold diethyl ether.

The crystalline powder samples of ML 3000 prepared according to the previously known methods were measured by means of X-rays in powder refractometers and the refractograms, the powder spectra, were compared with one another. The substance samples were additionally investigated using the differential scanning calorimetry method (DSC) or using the thermogravimetric method (TGA). The powder refractometry measurements and the DSC measurements show that after crystallization from diethyl ether the substance is initially formed as an ether solvate in the crystalline form of rods. On crystallization from ethyl acetate, a solvate with ethyl acetate is analogously formed in the form of rhombi. It has been shown that these solvates are unstable. They decompose in vacuo and/or at elevated temperatures with only incomplete release of the bound solvent to give largely amorphous substances which, however, still contain residual solvent and in which increased amounts of decomposition substances can be detected after drying. For the solvates, characteristic desolvation temperature changes are found by means of DSC technology.

Crude ML 3000, which is obtained as a potassium salt by the hydrazine process and which is then precipitated from the reaction mixture rendered acidic with mineral acid, also contains hydrazine, by-products and decomposition products (decarboxylation product and also dimer) as a contaminant in addition to the poorly water-soluble potassium salts. This necessitated additional purification operations. For example, to remove the hydrazine components, the crude crystalline acid thus had to be washed a number of times with dilute mineral acids or its solution had to be extracted in order to lower the hydrazine content in the pure substance into the range of harmless residual amounts.

None of the processes published up to now yielded a material unrestrictedly suitable for administration to humans.

The present invention is therefore based on the object of making available a process for the preparation of ML 3000 in which ML 3000 is obtained in high purity and pure, defined crystalline form.

Surprisingly, it has now been found that this object is achieved if the corresponding pyrrolizine compound is reacted with oxalyl chloride and hydrazine and the reaction product is subjected to a special work-up. Moreover, it has been found that during the work-up a novel polymorphous ML 3000 (polymorph A) is formed.

The present invention therefore relates to a process for the preparation of the compound of the formula I (ML 3000)

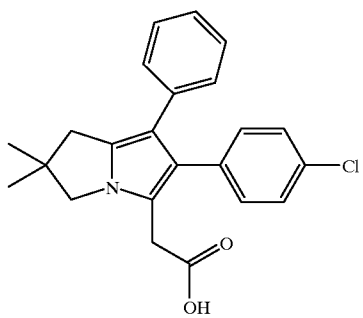

where the compound of the formula III

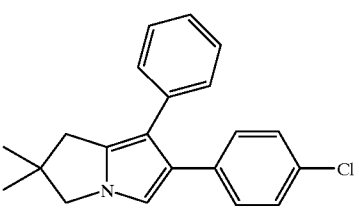

is reacted with oxalyl chloride and the product obtained is treated with hydrazine and an alkali metal hydroxide in the aqueous phase at elevated temperature, after treatment is complete a three-phase system is produced by addition of an ether which is not miscible or only limitedly miscible with water and the compound of the formula I is obtained by acidifying the middle phase.

Figure 1:
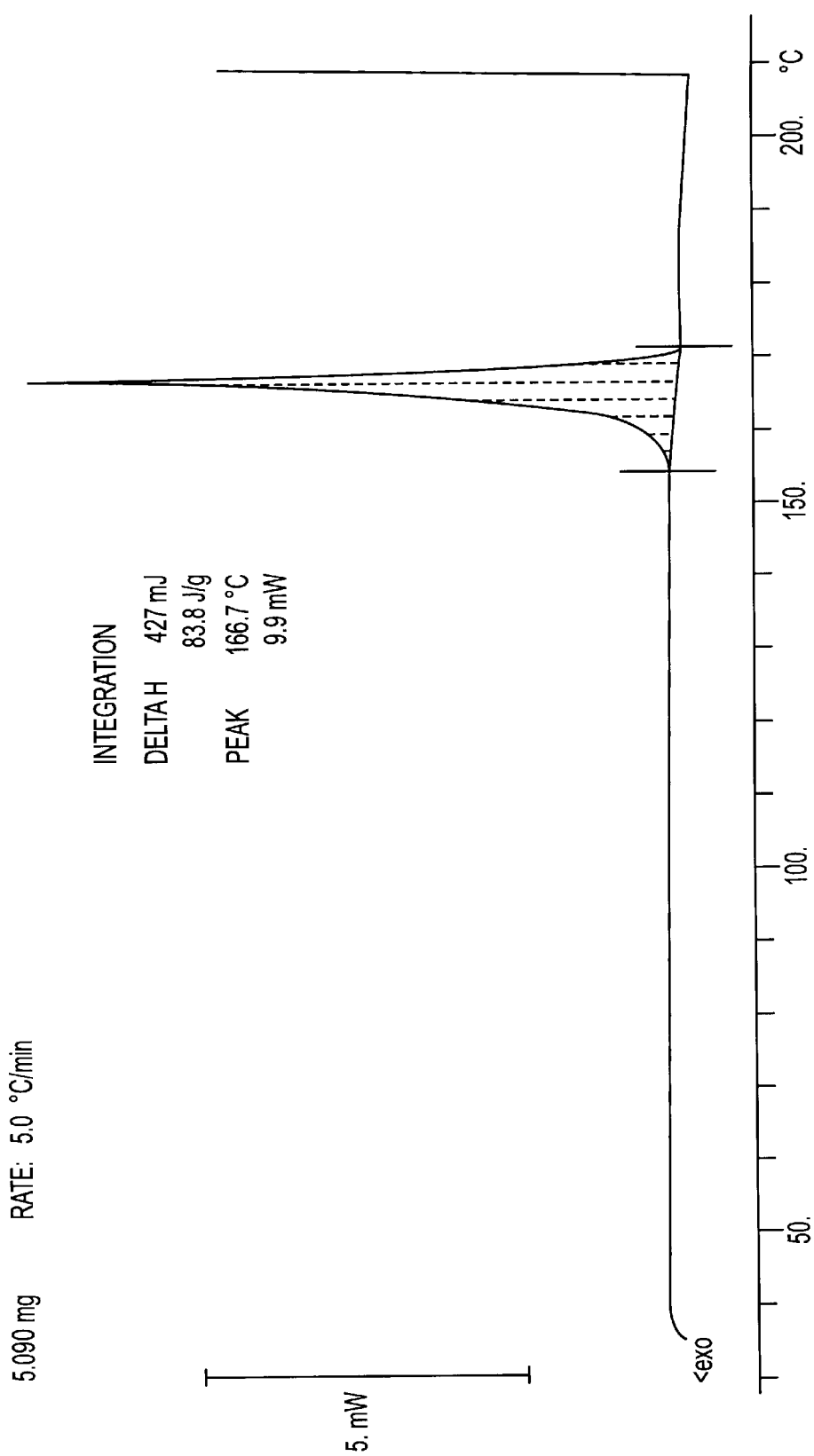
FIG. 1 shows the DSC diagram of a crystalline polymorph (polymorph A) of ML 3000.

The preparation of 6-(4-chlorophenyl)-2,2-dimethyl-7-phenyl-2,3-dihydro- 1H-pyrrolizin-5-yl-acetic acid (ML 3000) using the process according to the invention can be shown by the following reaction equations starting from the compound of the formula IV

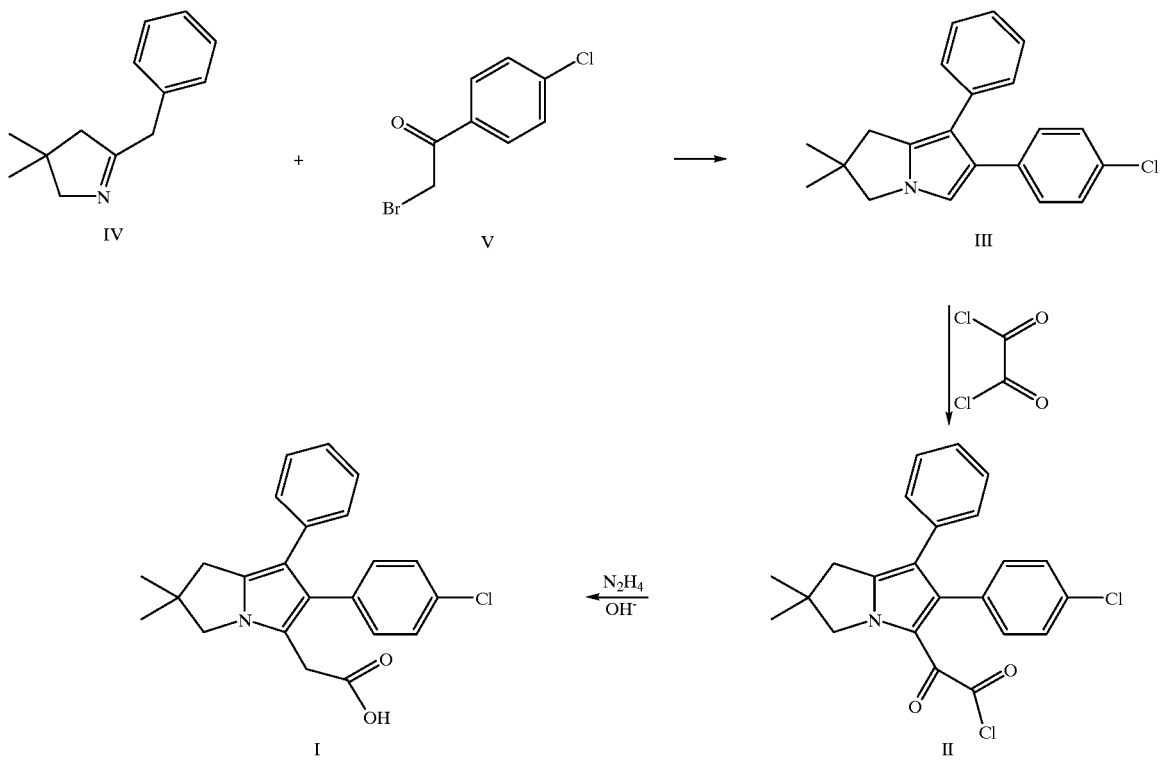

The compound of the formula IV is known. It is described, for example, in Arch. Pharm. 321, 159–162 (1988). It can be prepared by reaction of benzylmagnesium chloride with 3,3-dimethyl-4-chlorobutyronitrile, as is described [lacuna] J. Med. Chem. 37, 1894–1987 (1994). The reaction is carried out in an inert solvent, such as an ether or a hydrocarbon such as toluene. The compound of the formula IV is then reacted with an ω-bromo-4-chloroacetophenone V. The ω-bromo-4-chloracetophenone compound and its preparation are known, they are described, for example, in Bull. Soc. Chim. Fr. 21, 69 (1899).

The reaction is in general carried out in a polar organic solvent. Suitable polar organic solvents are, in particular, $C_1$–$C_4$-alcohols, such as methanol, ethanol, isopropanol or ethers, such as diethyl ether, THF, or dioxane. The reaction components can be employed in equimolar amounts. In general, however, the ω-bromo-4-chloracetophenone is used in an excess, for example in an amount of up to 40 mol %.

In order to trap the hydrogen bromide released in the reaction, it is carried out in the presence of a base. An inorganic base is preferably used, in particular an alkali metal hydrogencarbonate or alkali metal carbonate, the corresponding sodium and potassium compounds being particularly preferred. An inorganic base can be employed in the form of an aqueous solution. It has proven to be particularly preferred, however, to use an inorganic base in solid form. This facilitates the separation of the inorganic reaction products and reduces the by-product spectrum. An inorganic base is in general employed in equimolar amounts, based on the amount of hydrogen bromide released. Expediently, an inorganic base is used, however, in an excess, for example up to 1.8 equivalents. Moreover, it has proven expedient to carry out the reaction with exclusion of light. The reaction temperature can be varied within a wide range. It is preferably carried out, however, in the range from 0 to 50° C.

The compound of the formula III can be obtained in a customary manner by removing the salts formed and the solvent. The compound of the formula III is obtained in this way in a yield of at least 40% and with a purity of at least 97%. In particular, the content of the isomer having the 4-chlorophenyl group in the 5-position is not more than approximately 1.5% and in general approximately 1%.

The compound of the formula El is then reacted with oxalyl chloride. In general, an inert organic solvent such as an ether, in particular diethyl ether, methyl t-butyl ether, tetrahydrofuran or dioxane, a hydrocarbon, such as toluene, or a chlorinated hydrocarbon such as methylene chloride is used. The use of tetrahydrofuran is preferred.

In general, the reaction temperature is in the range from −20 to +30° C. In order to bring this about, the exothermic reaction is controlled by means of the addition rate of the oxalyl chloride and/or by cooling the reaction mixture. The compound of the formula II is obtained in this way.

The reaction mixture is then brought into contact with water in order to hydrolyze excess oxalyl chloride. Surprisingly, the hydrolysis of the compound of the formula II to the corresponding carboxylic acid does not occur here.

The reaction mixture is then treated with a reagent which is suitable for the reduction of the ketocarbonyl group in the 5-position with formation of the acetic acid group. The use of hydrazine (Wolff-Kishner reduction) is preferred for this purpose. The Huang-Minlon variant, in which the reaction with hydrazine is carried out in a high-boiling alcohol in the presence of an alkali metal hydroxide, has proven particularly expedient. A procedure is expediently used in which the solvent used for the reaction with oxalyl chloride is at least partially removed before or after addition of the high-boiling alcohol. Hydrazine, in particular hydrazine hydrate, is then added and the reaction temperature is increased to approximately 70–80° C. in order to remove any solvent which may remain by distillation. Following this, the reaction temperature is increased to 120 to 180° C., in particular 130 to 160° C. The alkali metal hydroxide is added in solid form or as a concentrated aqueous liquor, but preferably in solid form. The time of addition is not critical, expediently it is added after removal of the residual solvent used for the reaction with oxalyl chloride. Potassium hydroxide is preferably used.

As a high-boiling alcohol, an aliphatic mono- or dialcohol having a boiling point of at least 140° C. is in particular used. Suitable alcohols are ethylene glycol, ethylene glycol monomethyl ether, etc. and in particular diethylene glycol.

The reaction time is in general in the range from 30 to 300 minutes.

The constituents volatile at the reaction temperature, which are essentially water, hydrazine and possibly still residues of the solvent used for the reaction with oxalyl chloride, are expediently removed, for example by distillation.

After reaction is complete the reaction mixture is mixed with an ether (ethereal solvent) and with water or electrolyte-containing (e.g. NaCl-containing) water. An ether which is limitedly miscible with water is preferably used. Ethers which are utilizable are, for example, methyl t-butyl ether, tetrahydrofuran and in particular diethyl ether.

As a result of the addition of the ether, a 3-phase system is formed. The uppermost phase is an ether phase which contains the organic impurities present. The lowermost phase is a strongly alkaline aqueous phase which contains the inorganic constituents. The middle phase is an oily phase which essentially consists of the salt of ML-3000 with the alkali metal hydroxide used in the reaction, which is poorly soluble in the diethylene glycol-containing alkaline water phase. Surprisingly, it has been shown that the middle phase contains the salt of ML-3000 in high purity.

The phases are separated and the middle phase is treated with a mixture of water and an ether which is only limitedly miscible with water, e.g. diethyl ether or methyl t-butyl ether, and acidified to approximately pH 1 to 2 using an inorganic or organic acid, such as hydrochloric acid, sulfuric acid, phosphoric acid, acetic acid, oxalic acid or citric acid. The ML-3000 is then dissolved in the ether phase. If desired, this ether phase can then be subjected to further extraction steps with an acid or water in a customary manner. If desired, a further purification step by treating with active carbon or other adsorbents such as [sic] (e.g. bentonite etc.) can also be added.

The amount of ether and water which is added for the formation of the 3-phase system is not critical. In general, sufficient ether and water are used such that the phases form and can be separated in a simple manner. In general, 5 to 10 parts by weight of water and 3 to 20 parts by weight of ether are used per part by weight of starting compound.

The recovery of the ML-3000 from the ether phase can be carried out in different ways. For example, the ether can be evaporated and the ML-3000 recovered by crystallization from ethyl acetate or isopropanol. On evaporation of the ether a solvate of the ether crystallizes which in the case of diethyl ether contains 1 solvent molecule to 2 molecules of ML3000. From ethyl acetate, a corresponding solvate having one ethyl acetate molecule to 2 molecules of ML 3000 is obtained.

However, it is preferred to add at least one hydrocarbon boiling higher than the ether to the ether phase, if desired at least partially distilling off the ether and separating the ML-3000 precipitated in solid, crystalline form in the customary manner, e.g. by filtration or centrifugation, from the mother liquor and recovering it by drying in a gentle vacuum at slightly elevated temperatures. A hydrocarbon is preferably used which boils at least 30° C., in particular at least 40° C., higher than the ether. Sufficient hydrocarbon is used such that it is present in approximately a 2- to 15-fold excess (volume), if desired after distilling off the ether.

The hydrocarbon can be a straight-chain or branched aliphatic hydrocarbon preferably having 6 to 12 carbon atoms. Examples are n-hexane, n-heptane, n-octane, isooctane, n-decane, cyclohexane, cycloheptane. n-Heptane or a mixture of isomeric heptanes is preferred, and also cyclohexane.

Surprisingly, it has been shown that on treatment of an ethereal solution of ML 3000, e.g. the ether phase mentioned, with the hydrocarbon a novel, essentially solvent-free crystal modification of ML 3000, namely polymorph A, is obtained. Polymorph A has a sole endotherm in the DSC diagram (from 50° C. to 200° C.), which is in the range from 155 to 170° C. The DSC diagram is shown in FIG. 1.

Polymorph A can be obtained from amorphous ML 3000 or other crystal modifications thereof (polymorphs C and E, see examples 4 and 5) by treatment with the hydrocarbon at elevated temperature, e.g. at a temperature in the range from 40 to 110° C. The treatment with the hydrocarbon is expediently carried out by extracting with stirring (digesting).

Polymorph A further has the following significant peaks in the IR spectrum (trituration with KBr in the ratio 1:3; Spektrum 2000 FT-IR spectrometer from Perkin Elmer; control of the apparatus using the program Spektrum 2.00; the measurements were carried out in diffuse reflection): wavenumber ($cm^{-1}$): 1706; 1601; 1536; 1487; 1463; 1450; 1441; 1413; 1395; 1383; 1369; 1293; 1219; 1177; 1099; 1013; 836; 765; 698.

Figure 2:
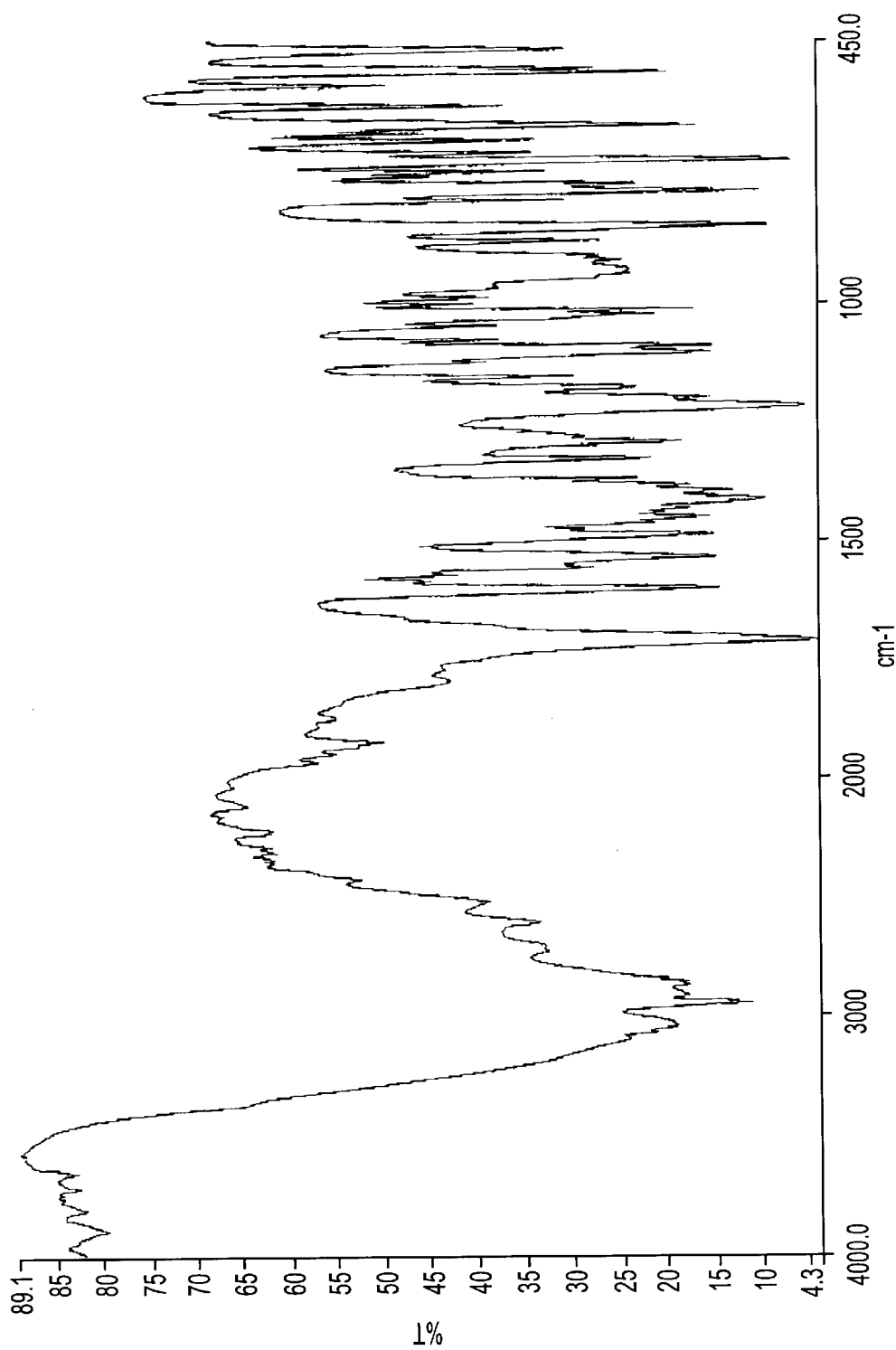
FIG. 2 shows the IR spectrum of polymorph A.

The IR spectrum is shown in FIG. 2.

Figure 3:
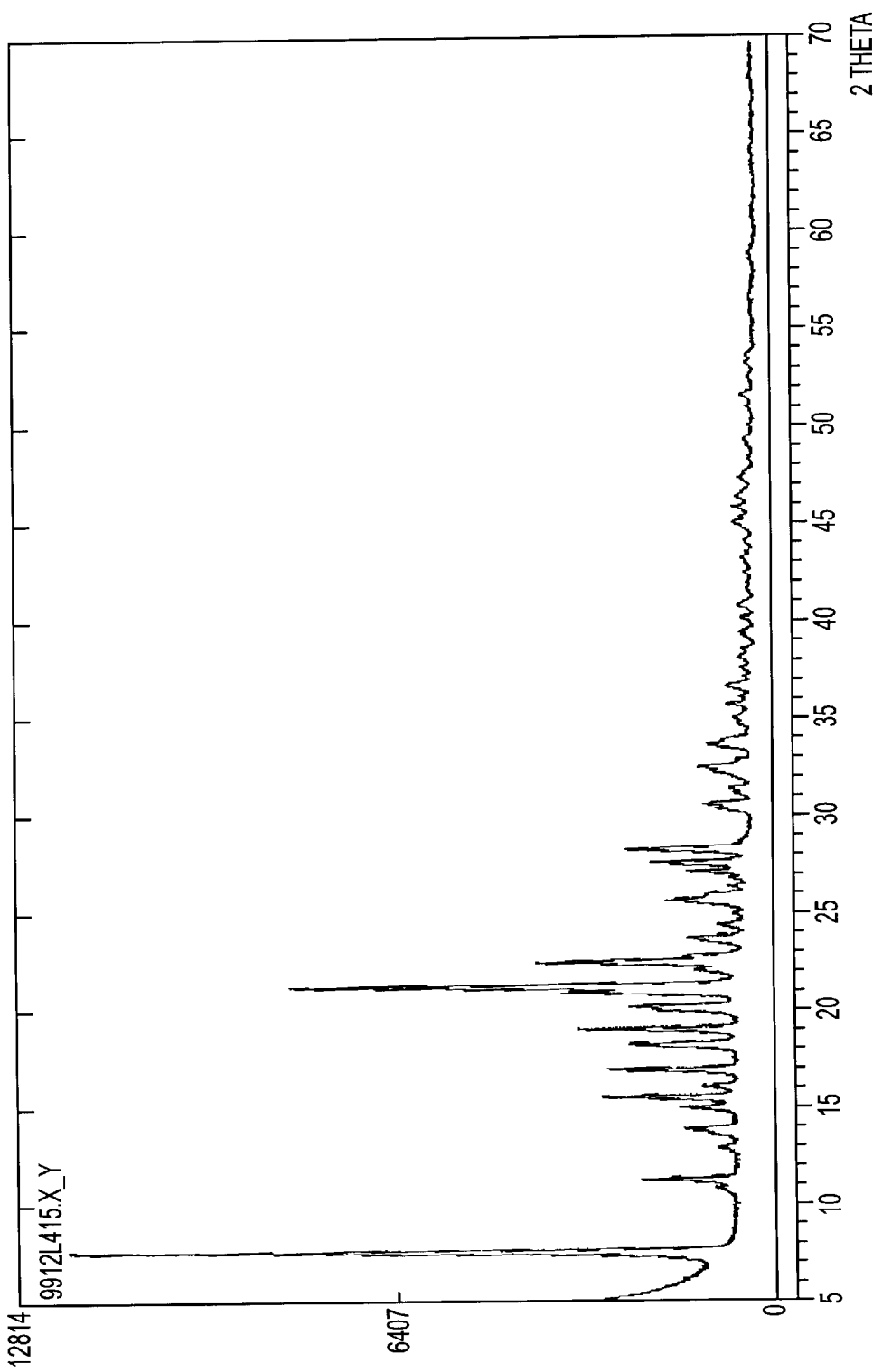
FIG. 3 shows the X-ray diffraction spectrum of polymorph A.

The X-ray diffraction diagram (powder refractogram) of polymorph A is shown in FIG. 3. Polymorph A has the following characteristic d values 11.9; 4.2; 4.0, (2 Θ; 7.5; 21.2; 22.4).

Polymorph A has a narrow particle size distribution, the mean particle size (determined by means of laser diffraction spectra on the system from Helios-Sympatec: Dry disperser RODOS; focal length 50 mm) being in the range from 30 to 50 $\mu$m. The solvates, however, have a wide particle size distribution having a high proportion of fine-grain material of approximately 10 $\mu$m and a high coarse-grain content of approximately 1 mm, the mean particle size is in the range from approximately 100 to 150 $\mu$m.

In comparison to the known solvates and the amorphous form of ML 3000, polymorph A has significant advantages. On account of the crystalline structure polymorph A is stable on drying and storage. No phase transitions and no secondary aggregation are to be observed as in the case of the amorphous form. Moreover, the purity of polymorph A is higher, because during recovery no impurities are included in the crystal structure.

Polymorph A has a compact crystal system with a relatively small surface area. Surface phenomena, such as electrostatic charge, adhesion, adsorption etc., only occur to a small extent in comparison with amorphous ML 3000. The crystal structure moreover requires a high chemical stability, whereas the amorphous ML 3000 has a high surface area and is therefore subject to relatively severe oxidative decomposition.

The solvates are not stable on storage, because they themselves release solvent at room temperature. The phase transition taking place in the course of this into the solvent-free, amorphous form does not proceed unequivocally. During the aging of the solvates, cavities remain in the crystal system. The substance is thereby subject to relatively severe oxidative degradation. Moreover, during aging a product having a wide particle size distribution is obtained, which unfavorably influences its flow properties and its further processability.

In the process according to the invention, ML-3000 is obtained in excellent yield of at least 70%, starting from the compound of the formula III. This means a considerable improvement compared with the prior art. According to example 5C of WO95/32971, a compound analogous to ML-3000 is obtained in only 29% [lacuna]. Surprisingly, ML-3000 is obtained in high purity in solvent-free crystalline form. The concentration, determined by means of tetrabutylammonium hydroxide titration, is 100%. The concentration of heavy metals is <10 ppm and the amount of ash is 0%. The sum of isomers and derivatives of ML-3000 is <0.2% (determined by means of HPLC), the concentration of residual solvent is under 0.2% (determined by the head space gas chromatography method).

The compound according to the invention (polymorph A) has proven to be a potent cyclooxygenase and/or lipoxygenase inhibitor. It is distinguished by a strong analgesic action and by a uniform inhibitory action on the enzymes cyclooxygenase (CO) and lipoxygenase (LO) ($IC_{50}LO/IC_{50}CO\sim1$). It is therefore utilizable in the treatment of disorders which are accompanied by a change in the metabolism of arachidonic acid. In particular, mention may be made of disorders of the rheumatic type and the prevention of allergically induced disorders. The compound according to the invention is thus an efficacious antiinflammatory, analgesic, antipyretic and antiallergic and has an antibronchoconstrictor activity and is moreover utilizable for thrombosis prophylaxis and for the prophylaxis of anaphylactic and septic shock and also for the treatment of dermatological disorders, such as psoriasis, urticaria, acute and chronic exanthema of allergic and nonallergic origin. It is moreover utilizable for the treatment of hypercholesterolemia.

The compound according to the invention can be administered either as an individual therapeutic active compound or as a mixture with other therapeutic active compounds. It can be administered as such, but in general it is administered in the form of a pharmaceutical composition, i.e. as a mixture of the active compound with pharmaceutically acceptable excipients, in particular vehicles or diluents and/or additives. The compound or the composition can be administered enterally, e.g. orally or rectally, or parenterally, e.g. subcutaneously, intravenously or intramuscularly, but they are preferably given in oral dose forms.

The type of pharmaceutical composition and of pharmaceutical carrier or diluent depends on the desired type of administration. Oral compositions can be present, for example, as tablets or capsules and can contain customary excipients, such as binders (e.g. syrup, acacia, gelatin, sorbitol, tragacanth or polyvinylpyrrolidone), fillers (e.g. lactose, sugar, cornstarch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations can be present in the form of aqueous or oily suspensions, solutions, emulsions, syrups, elixirs or sprays etc. and can be present as a dry powder for reconstitution with water or another suitable carrier. Liquid preparations of this type can contain customary additives, for example suspending agents, flavorings, diluents or emulsifiers. For parenteral administration, solutions or suspensions with customary pharmaceutical carriers can be employed.

Treatment with the compound according to the invention takes place by administering an efficacious amount of the compound, as a rule formulated according to pharmaceutical practice, to the individual to be treated, preferably a mammal, in particular a human. Whether such a treatment is indicated and in what form it has to take place depends on the individual case and is subject to medical assessment (diagnosis), the signs, symptoms and/or dysfunctions present and risks of developing specific signs, symptoms and/or dysfunctions, and additionally includes further factors.

As a rule, treatment is carried out by single or repeated daily administration, if appropriate together or alternatively with other active compounds or active compound-containing preparations, so that an individual to be treated is administered a daily dose of approximately 0.1 mg to approximately 1000 mg and in particular 0.5 mg to approximately 100 mg per kg of body weight.

The following examples illustrate the invention without restricting it.

The DSC diagrams and X-ray diffraction spectra (powder refractograms) indicated in the context of the present invention were obtained as follows:

The DSC analyses were carried out using the TA 4000 system from Mettler (measuring cell DSC-20; processor T11; analysis using program TA-72). The heating rate was 5° C./min, in the melting range 2° C./min.

The powder refractograms were determined using an STOE powder diffraction system powder diffractometer from Stoe, Darmstadt, using monochromatic CuK$\alpha$1 radiation.

EXAMPLE 1

6-(4-Chlorophenyl)-2,2-dimethyl-7-phenyl-2,3-dihydro-1H-pyrrolizine 4.64 kg (190.9 mol) of magnesium and 18.8 kg of diethyl ether are introduced successively, after evacuating and passing in N2 three times, into a 250 l reactor. The ether is brought to reflux. With the stirrer switched off, 0.03 kg of iodine and 0.5 kg (4 mol) of benzyl chloride are added, whereupon the reaction of the magnesium with the halide starts immediately (decolorization and turbidity). With the stirrer switched on, a solution of 23.5 kg (185.6 mol) of benzyl chloride in 37.8 kg of diethyl ether is added from a supply vessel during the course of 2 h, the black-gray mixture refluxing vigorously. After addition is complete, the Grignard solution is kept at reflux for a further 2 h. A solution of 17.7 kg (134.6 mol) of distilled 4-chloro-3,3-dimethylbutyronitrile in 48.5 kg of diethyl ether is then added at reflux temperature from the supply vessel in the course of 1.5 h. The reaction mixture is heated to reflux for a further 2 h. The diethyl ether is then distilled off from the pale gray suspension at normal pressure. 54–59 kg of distillate are removed (time required 2 h), such that the reaction mixture still remains stirrable.

106.3 kg of toluene are added to the residue. The internal temperature is 43° C. An ether/toluene mixture is then distilled off until an internal temperature of 85–90° C. is reached (about 36–40 kg of distillate).

The residue becomes a thick, but still stirrable suspension without a crust. This suspension is transferred to a reactor into which 76.7 kg of ice and 38.5 kg of 32% strength hydrochloric acid have been introduced beforehand. On entry, the internal temperature of the phases rises from 0 to 23° C. The pH of the water phase should be between 0.5 and 1.5 (pH=1.0). After warming the reactor to an internal temperature of 40–45° C., the phases are vigorously stirred with one another for 1.75–2 h. They are then allowed to stand at this temperature and with the stirring switched off for 10–15 min for phase separation. The water phase containing the product is separated off (147 kg).

The water phase is cooled to −8 to 0° C. in an extraction apparatus and then basified with 33.2 kg of 24% strength ammonia, the supply rate of the ammonia being controlled such that the internal temperature does not exceed a maximum of 5° C. The pH is 10.5–11.

The basified water phase is thoroughly stirred with 106.3 kg of diethyl ether for 30–40 min at 10–25° C. and then allowed to stand for 25–30 min for phase separation. The clear, slightly yellow water phase (170 kg) is separated off and discarded. The clear, yellowish-green ether phase is completely concentrated in vacuo (0.7–0.8 mbar), 95 kg of ether distillate being obtained (1.40 h). As a distillation residue, 20.6 kg of pale green oil is obtained, which contains 86.7% of 2-benzyl-4,4-dimethyl-1-pyrroline. 20.6 kg of the residue (86.7% strength), corresponding to 17.9 kg (95.5 mol) of 2-benzyl-4,4-dimethyl-1-pyrroline, 29.7 kg (127.2 mol, 1.33 equiv.) of ω-bromo-4-chloroacetophenone and 226.6 kg of methanol are introduced into a reactor (500 l). After addition of 12.7 kg (151.2 mol, 1.58 equiv.) of sodium hydrogencarbonate, the mixture is stirred with exclusion of light at 17–24° C. with formation of a beige suspension. The reaction is continued until the residual content of pyrroline compound in the mixture is <5%. After 17 h, a sample is taken and tested for the content of pyrroline compound by means of gas chromatography. The analysis showed a concentration of 2%. The suspension is then centrifuged at an internal temperature of 18–22° C. and the solid obtained by centrifugation is washed out using 14.4 kg of methanol in two portions. The still moist, slightly yellow product weighs 25.8 kg.

The still moist crude product (25.8 kg) is suspended in 150 kg of water then warmed to an internal temperature of 50–60° C. in the course of 15 min and stirred at this temperature for 40 min. The suspension, cooled to 40° C. (40 min), is centrifuged and the pale yellow, crystalline solid obtained by centrifugation is subsequently washed with 27 kg of water in 2 portions. The product is dried in vacuo at 50–60° C. for 12–24 h. 18.6 kg of 6-(4-chlorophenyl)-2,2-dimethyl-7-phenyl-2,3-dihydro-1H-pyrrolizine are obtained, having a content of 0.33% of ash and an isomer content of (5-(4-chlorophenyl)-2,2-dimethyl-7-phenyl-2,3-dihydro-1H-pyrrolizine) of 1.0%.

EXAMPLE 2

6-(4-Chlorophenyl)-2,2-dimethyl-7-phenyl-2,3-dihydro-1H-pyrrolizin-5-ylacetic Acid (ML-3000)

After evacuating and passing in N2 three times, 11.5 kg (35.7 mol) of 6-(4-chlorophenyl)-2,2-dimethyl-7-phenyl-2,3-dihydro-1H-pyrrolizine in 60 kg of tetrahydrofuran (THF) are introduced into a 250 l reactor. The yellow-colored solution is cooled to 10–15° C. under a 0.5 bar nitrogen supply (N2). 6.8 kg (54.7 mol) of oxalyl chloride are then metered in from a supply vessel under N2 over the course of 35 min such that the internal temperature does not exceed 20° C.

After addition is complete, the now dark-green, thin suspension is stirred at an internal temperature of 18–25° C. for 20–30 min. 18 kg of ice are introduced into a 500 l reactor in flakes. The warm suspension (25° C.) is added to this ice over the course of 5 min such that the internal temperature of the mixture does not exceed 20° C.

The reaction mixture is stirred at an internal temperature of 25–35° C. for a further 10–20 min. The still green solution is diluted with 62.2 kg of diethylene glycol at 25–35° C. 14.9 kg (298 mol) of hydrazine hydrate are then added from a supply vessel during the course of 10–15 min. The internal temperature rises to at most 40–45° C. By increasing the temperature stepwise during the course of 1.5 h, the now beige-colored suspension is heated to an internal temperature of 70–75° C., THF being distilled off. 45.4 kg of THF distillate are collected until an internal temperature of 75° C. is reached.

The reaction mixture is cooled to 50–55° C. and treated with a total of 26.4 kg of potassium hydroxide in flakes (KOH) in 8 to 10 portions divided over the course of 45 min, the internal temperature already rising to 65–70° C. with the first 5 kg of KOH and the initially thick suspension turning yellow, becoming highly liquid and gentle reflux occurring short-term.

This suspension is now heated to 90° C. with a temperature increase of 15° C./h, slight foaming commencing from 85° C. and the suspension thickening. With a temperature increase of 2° C./h, the internal temperature is now further raised to 102° C. and at the same time nitrogen is blown through the reaction mixture through the dip tube at an increased stirrer speed. As a result of strong foaming and additional evolution of gas, the volume of the reactor contents increases to double. If required, the reaction temperature is lowered by cooling. At an internal temperature of 100–105° C., the foam begins to collapse and a red-brown thin suspension is formed, which is now heated further to an internal temperature of 140–145° C. at a heating rate of 15° C./h. In the case of excessive foaming, the reaction temperature is briefly lowered by cooling. At the same time, a number of aqueous distillates of 44 kg in total are collected.

The batch is kept at 120–145° C. for 2 h–2.5 h. The reactor temperature is then cooled to 30–40° C. and 74.7 kg of water and 56.7 kg of diethyl ether are added. The reaction mixture is carried out at an internal temperature of 30–33° C. for 10–15 min, then the phases are allowed to settle. The resulting three-phase system is separated. The lowermost strongly alkaline aqueous phase, which weighs 154.9 kg, is colorless and only slightly turbid. It is disposed of as wastewater. The yellow-colored, turbid intermediate phase of oily consistency weighs 29.6 kg and contains the main amount of product as potassium salt. The uppermost, clear, yellow-colored ethereal phase is vigorously stirred in an extraction apparatus with 10 kg of water for 10 min at an internal temperature of 30° C. The water phase is separated off 10 min after switching off the stirring. The intermediate phase (29.6 kg) and the aqueous extract of the ether phase (10.9 kg) are mixed with 126.2 kg of diethyl ether and 59.7 kg of water in an extraction apparatus and the mixture is cooled to an internal temperature of 0–5° C.

By means of a supply vessel, a mixture of 6.0 kg of 32.5% strength hydrochloric acid and 6.0 kg of water is now metered in during the course of 15 min such that a maximum internal temperature of 10° C. is not exceeded and a pH of 1–2 is reached. If this pH is not reached, a further 0.2 kg of 32.5% strength hydrochloric acid as a mixture with 0.2 kg of water is added. After reaching this pH, the phases are thoroughly stirred for a further 5–10 min, and then allowed to stand for 10–20 min with the stirring switched off for phase separation.

The HCl-acidic water phase is drawn off. The ether phase is again treated with a mixture of 9.5 kg of hydrochloric acid and 19 kg of water via the supply vessel and thoroughly stirred at an internal temperature not exceeding 10° C. for 5–10 min. The phases are separated and the HCl treatment is repeated up to 3 times if desired.

The ether phase is then treated with 30 kg of demineralized water, thoroughly stirred for 10–20 min and warmed to 15–20° C. The phases are separated and the extraction is repeated.

The ether phase, washed free of traces of acid, is treated with 6.5 kg of anhydrous magnesium sulfate and 0.4 kg of active carbon (Acticarbon 2S), which are suspended in 1 kg of diethyl ether, and stirred at 18° C. for 30–45 min. The suspension is subjected to clarifying filtration through a pressure filter coated with 0.5 kg of filter aid (Cell Flock) in a distillation apparatus. The filter and apparatus are then rinsed with 8 kg of diethyl ether.

95.6 kg of n-heptane are added to the ether phase and the ether is distilled off in vacuo at an internal temperature of 15–20° C. The crystal suspension resulting after distilling off the ether is cooled to an internal temperature of 13–18° C. and stirred at this temperature for 0.5–1.5 h, then the crystals are removed by centrifugation. The moist product obtained is washed with 23.0 kg of n-heptane in 2 portions. The moist product is dried overnight in a vacuum drying oven at 50–60° C. and, if desired, ground. 10.5 kg (77.2%) of ML-3000 are obtained.

Description of the Product

The product has a slightly yellowish to ivory-colored coloration. The solution in tetrahydrofuran is colorless (Y7) and clear. The melting point, determined by the DSC method (under conditions other than indicated above) is 157° C. A second determination of the melting point under the conditions indicated above has yielded the DSC diagram shown in FIG. 1.

The IR spectrum and the powder refractogram is shown in FIGS. 2 and 3. The lattice distances (d values) are as follows (all peaks up to 2 Θ=34 were taken into account):

| 2 Θ | d value | rel. intensity (%) |
|---|---|---|
| 7.5 | 11.9 | 100.0 |
| 10.8 | 8.2 | 8.3 |
| 11.2 | 7.9 | 18.6 |
| 13.8 | 6.4 | 12.6 |
| 14.9 | 5.9 | 12.7 |
| 15.4 | 5.8 | 24.2 |
| 15.9 | 5.6 | 10.0 |
| 16.8 | 5.3 | 23.4 |
| 18.1 | 5.0 | 20.1 |
| 18.15 | 4.9 | 20.1 |
| 19.0 | 4.7 | 27.4 |
| 19.9 | 4.5 | 16.8 |
| 20.1 | 4.4 | 20.2 |
| 20.8 | 4.3 | 30.0 |
| 21.2 | 4.2 | 68.5 |
| 22.0 | 4.05 | 10.8 |
| 22.4 | 4.0 | 33.3 |
| 22.8 | 3.9 | 12.5 |
| 23.7 | 3.7 | 11.9 |
| 24.4 | 3.6 | 7.7 |
| 25.0 | 3.55 | 5.4 |
| 25.7 | 3.5 | 14.8 |
| 26.4 | 3.4 | 6.0 |
| 26.9 | 3.3 | 6.0 |
| 27.2 | 3.25 | 11.8 |
| 27.7 | 3.2 | 17.0 |
| 28.4 | 3.1 | 20.2 |

-continued

| 2 Θ | d value | rel. intensity (%) |
|---|---|---|
| 30.4 | 2.95 | 7.8 |
| 30.7 | 2.9 | 9.4 |
| 31.2 | 2.85 | 5.1 |
| 31.5 | 2.8 | 5.8 |
| 32.3 | 2.75 | 8.6 |
| 32.5 | 2.7 | 10.2 |
| 33.7 | 2.65 | 9.0 |
| 33.9 | 2.6 | 7.0 |

The content, determined by tetrabutylammonium hydroxide titration, is 100.9%.

Content of heavy metals: <10 ppm.

Ash content: 0%

Content of residual solvents (determined by GC): 0.11% of diethyl ether and 0.04% of heptane Hydrazine content: <0.3 ppm.

EXAMPLE 3

Preparation of Polymorph A of 6-(4-chlorophenyl)-2,2-dimethyl-7-phenyl-2,3-dihydro-1H-pyrrolizin-5-ylacetic Acid by Crystallization from Diethyl Ether/Cyclohexane The water-moist crude 6-(4-chlorophenyl)-2,2-dimethyl-7-phenyl-2,3-dihydro-1H-pyrrolizin-5-ylacetic acid (500 g) is completely dissolved in diethyl ether (13 l) with stirring at elevated temperature (40–50° C.), filtered through alumina Al2O3 and the solvent is removed from the filtrate. The crude crystal fraction obtained as a residue is suspended in cyclohexane (3.6 l) and digested in the presence of heat. After cooling to room temperature, the crystals are filtered off, washed with cold cyclohexane, then with cold methanol and then dried at 50–60° C. for a number of hours. 470 g (73% with respect to the precursor employed) of polymorph A of 6-(4-chlorophenyl)-2,2-dimethyl-7-phenyl-2,3-dihydro-1H-pyrrolizin-5-ylacetic acid are obtained in 99.69% purity.

EXAMPLE 4

Preparation of 6-(4-chlorophenyl)-2,2-dimethyl-7-phenyl-2,3-dihydro-1H-pyrrolizin-5-ylacetic Acid·½ Ethyl Acetate (Polymorph C)

The crude 6-(4-chlorophenyl)-2,2-dimethyl-7-phenyl-2,3-dihydro-1H-pyrrolizin-5-ylacetic acid (33 kg) suspended in ethyl acetate (115 l) at elevated temperature (40–50° C.) is brought into solution under reflux. The now clear solution is filtered through a heated filter funnel and then slowly cooled to 15–20° C. with stirring in the course of 2–2.5 h at a cooling rate of 0.5° C./min. The crystals are allowed to deposit at this temperature with the stirring switched off for 20 min, are centrifuged and are washed with cold ethyl acetate (33 l). The content of ethyl acetate was determined by means of 1H-NMR-(CDCl3) from the crystal fractions freshly obtained after squeezing off and air-drying. The expected theoretical value of 10.38 percent by weight (%) for the 2:1 solvate (hemisolvate) was approximately achieved. From the integral above the resonance line for the acetyl methyl group of the ethyl acetate (d=2.04, 3H) to the integral above the resonance line of the methylene group of the ML 3000 at d (ppm)=2.85, (2 H) the numerical ratio of 3:4 to be expected results for the hemisolvate.

Figure 4:
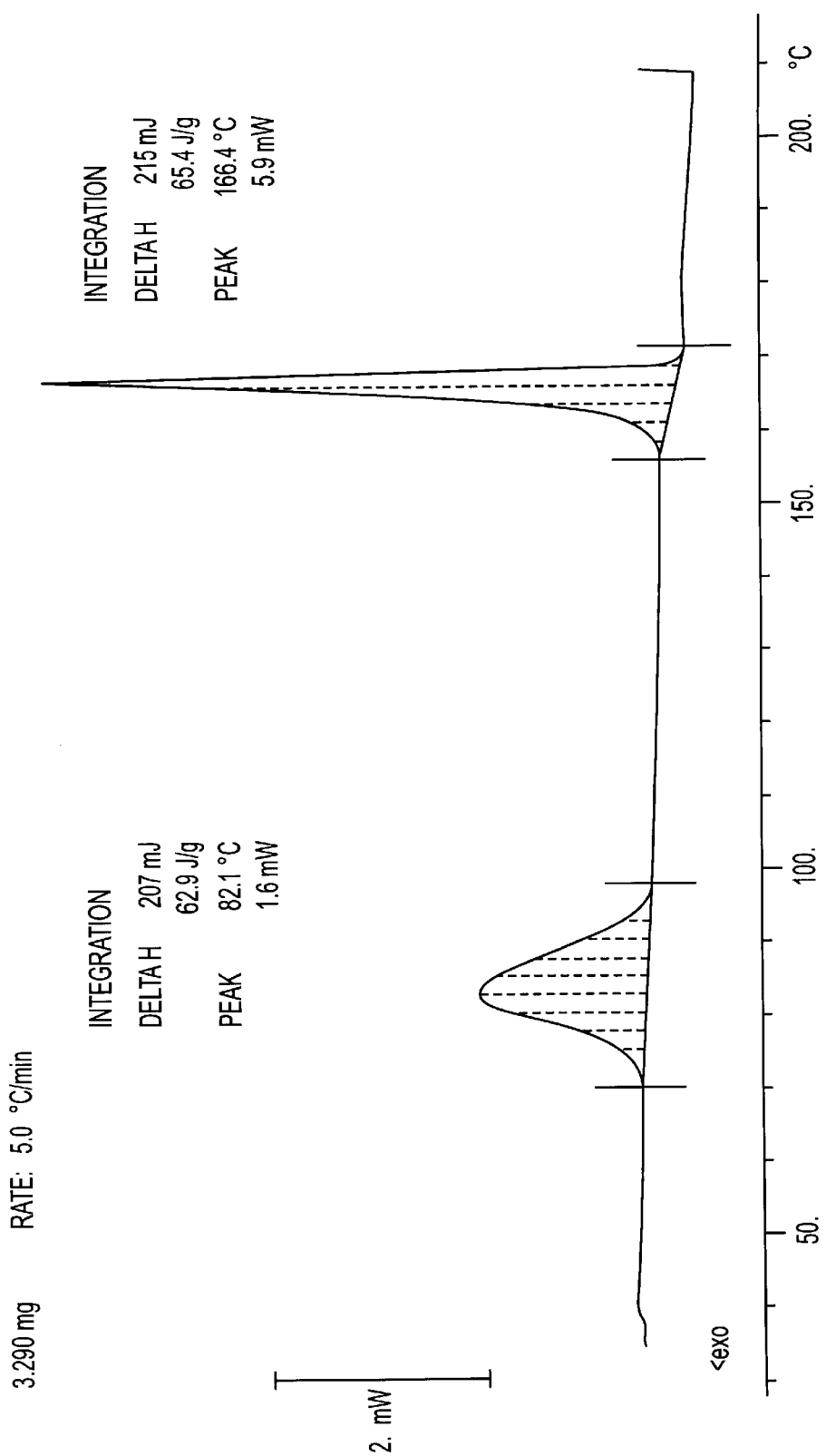
FIG. 4 shows the DSC diagram of the ethyl acetate solvate of ML 3000 (polymorph C).
Figure 5:
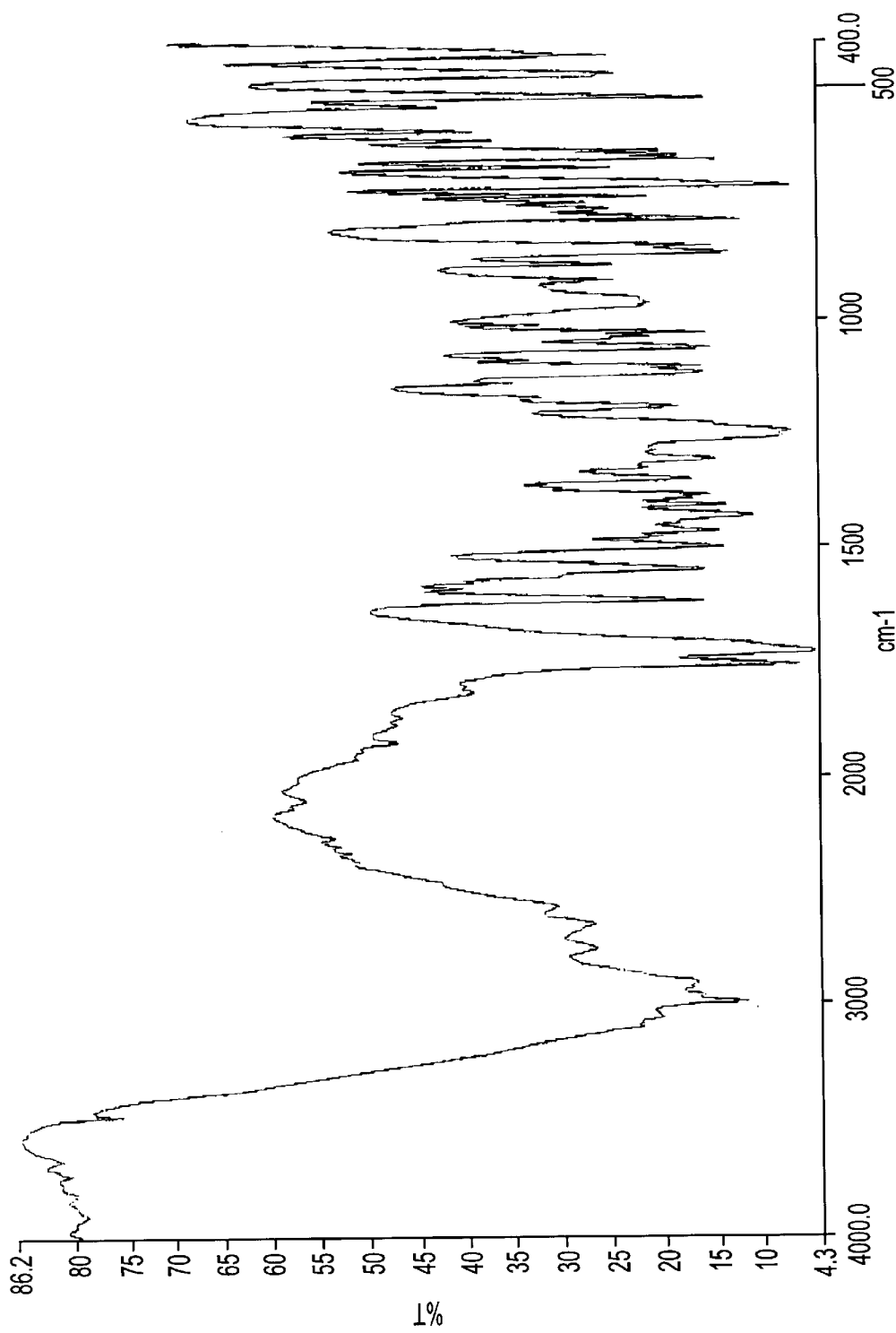
FIG. 5 shows the IR spectrum of polymorph C.
Figure 6:
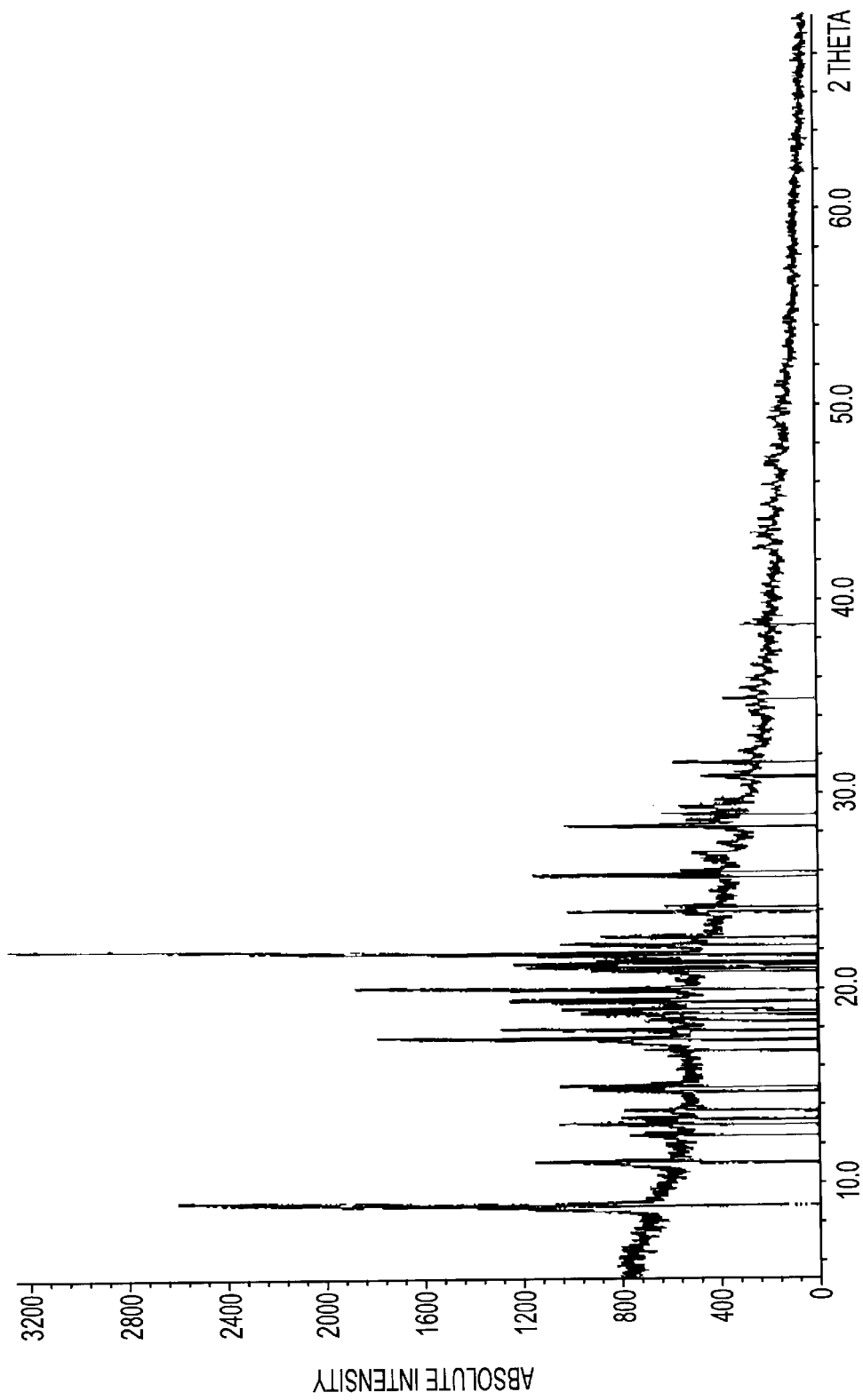
FIG. 6 shows the X-ray diffraction diagram of polymorph C.

The DSC diagram, the IR spectrum and the powder refractogram are shown in FIGS. 4, 5 and 6.

EXAMPLE 5

Preparation of 6-(4-chlorophenyl)-2,2-dimethyl-7-phenyl-2,3-dihydro-1H-pyrrolizin-5-ylacetic Acid·½ Diethyl Ether (Polymorph E)

6-(4-Chlorophenyl)-2,2-dimethyl-7-phenyl-2,3-dihydro-1H-pyrrolizin-5-ylacetic acid (2 g) are dissolved completely in diethyl ether (36 ml) under reflux. With exclusion of light, the solution is slowly cooled to room temperature over the course of 7 hours. On further lowering of the temperature to 0° C., the formation of crystals takes place from 15° C. For crystal growth, the solution was stored at 0° C. for 2 days, then the mother liquor was decanted from the crystals.

The content of diethyl ether was determined by means of 1H-NMR-(CDCl$_3$) from the crystals freshly obtained after decantation and air-drying. The expected theoretical value of 8.87 percent by weight (%) for the 2:1 solvate (hemisolvate) was approximately achieved. From the integral above the triplet for the ethyl methyl groups of the diethyl ether ($\delta$=1.21, 6H) to the integral above the resonance line of the geminal dimethyl group of ML 3000 ($\delta$=1.29, 6 H), the expected numerical ratio of 1:2 results for the hemisolvate.

Figure 7:
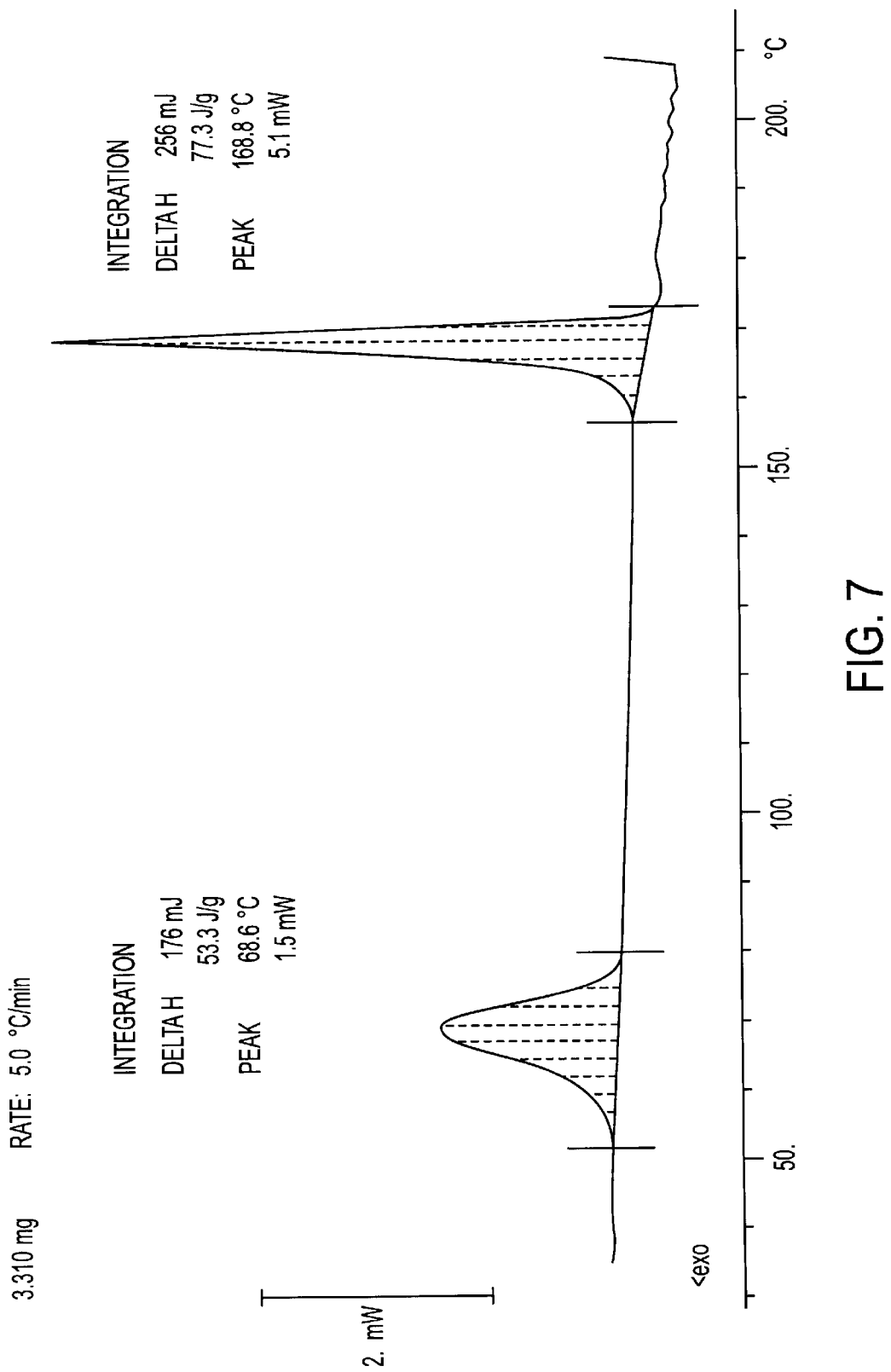
FIG. 7 shows the DSC diagram of the di ethyl etherate of ML 3000 (polymorph E).
Figure 8:
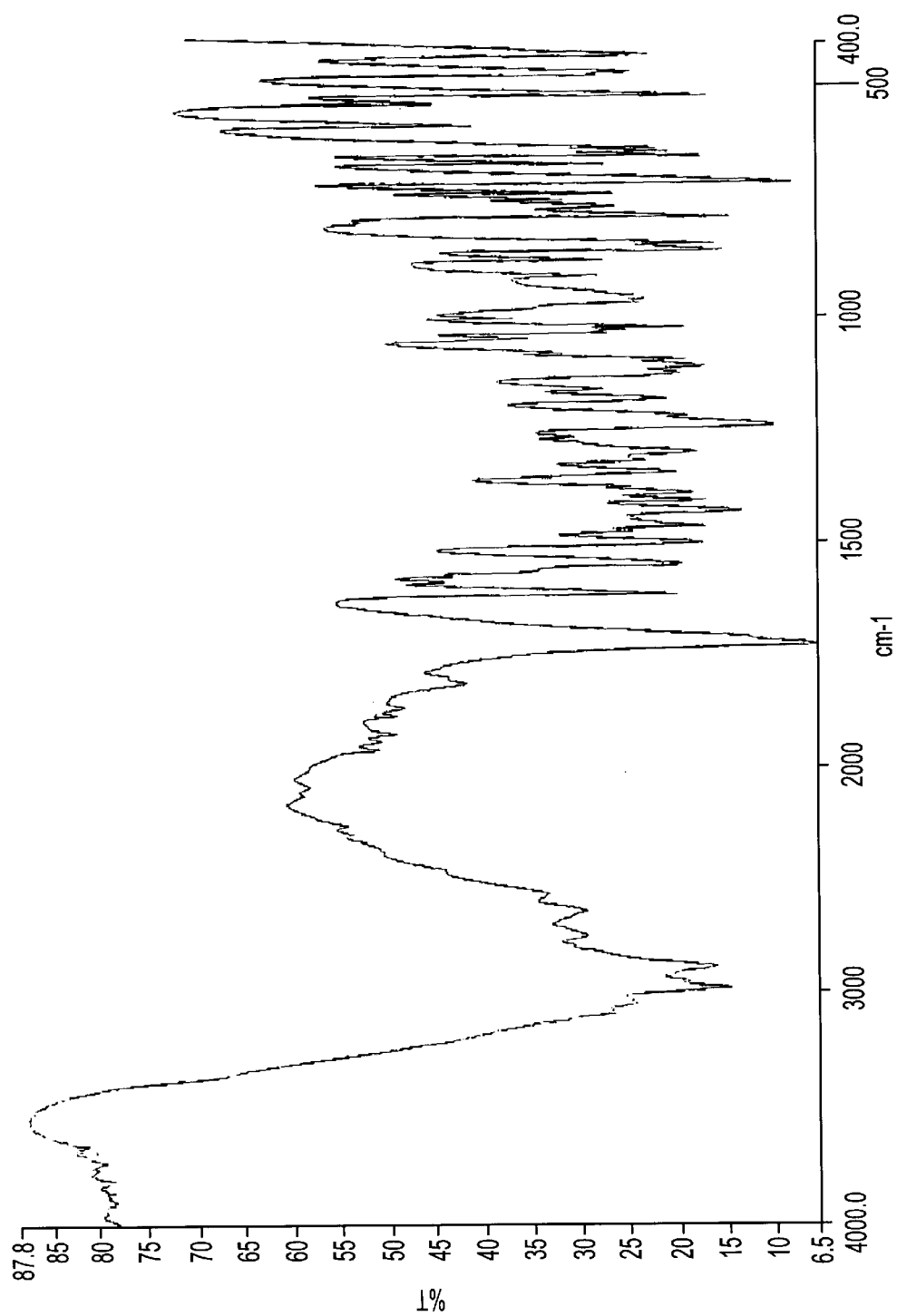
FIG. 8 shows the IR spectrum of polymorph E.
Figure 9:
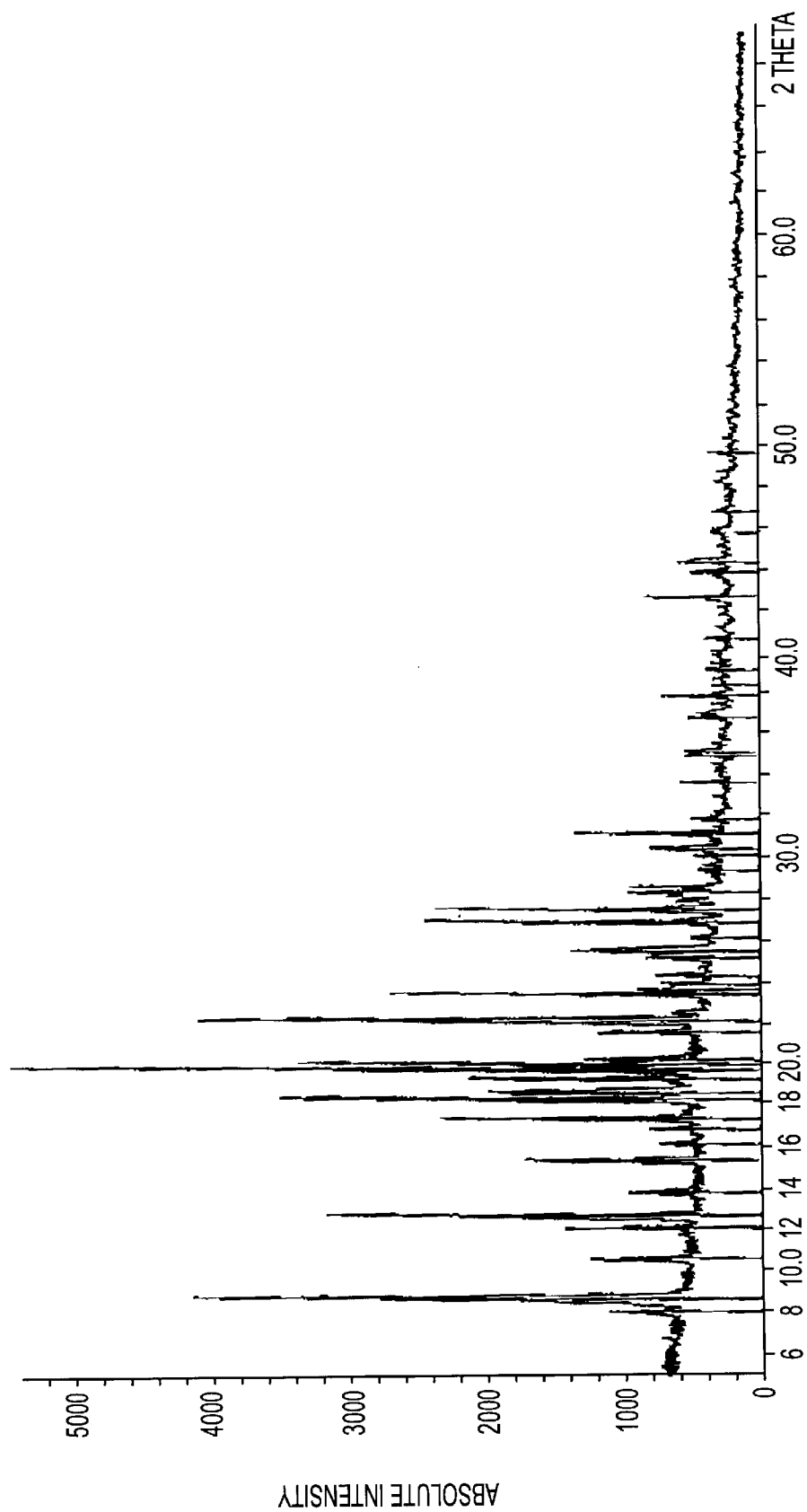
FIG. 9 shows the X-ray diffraction diagram of polymorph E.

The DSC diagram, IR spectrum and the powder refractogram are shown in FIGS. 7, 8 and 9.

EXAMPLE 6

Preparation of Single Crystals of the Polymorph E 6-(4-Chlorophenyl)-2,2-dimethyl-7-phenyl-2,3-dihydro-1H-pyrrolizin-5-ylacetic acid (250 mg) are dissolved in diethyl ether (5 ml) with addition of 1,4-dichlorobenzene (0.5 ml). With exclusion of light, the solution was cooled for one hour at 4° C., then to –25° C. The substance crystallizes in the course of one day in the form of large, well-formed colorless rods.

EXAMPLE 7

Preparation of Polymorph A of 6-(4-chlorophenyl)-2,2-dimethyl-7-phenyl-2,3-dihydro-1H-pyrrolizin-5-ylacetic Acid by Crystallization from Methyl Tert-butyl Ether (MTB)/n-heptane ML 3000 (1 g) is suspended in methyl tert-butyl ether (14 ml) in a 100 ml two-necked flask which is equipped with a reflux condenser and magnetic stirring bar and is wrapped with aluminum foil for protection against the incidence of light and is completely dissolved by heating to boiling temperature under an argon atmosphere (1.2 atm). After stirring (200 rpm) under reflux for 15 minutes, n-heptane is added to the clear solution until the beginning of turbidity (30 ml) then further n-heptane (40 ml) is added slowly in the presence of heat until the formation of a suspension (65° C.), which is then allowed to cool to room temperature with stirring. After 3 hours, the suspension is stored at 4° C. for a further 15 hours in a refrigerator. The crystals are filtered off with suction from the mother liquor through a G4 glass sinter filter using a mild vacuum (500 mbar). The crystal cake is resuspended repeatedly (5 times) in n-heptane (10 ml) and sucked dry (1 min) and then stored in a sealed jar without further drying. The yield of crystals is 81%, they are of pure white color. The crystals show the powder refractogram of pure polymorph A.

What is claimed is:

1. A process for the preparation of a compound of Formula I

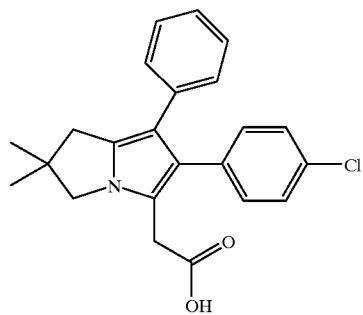

comprising reacting a compound of Formula III

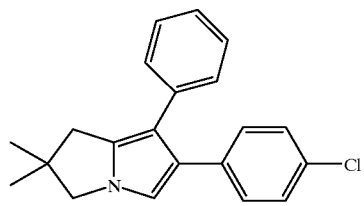

with oxalyl chloride so as to obtain a product, reduction of said product with hydrazine and an alkali metal hydroxide in an aqueous phase at elevated temperature so as to form a treated product, adding an ether to the treated product so as to form a three-phase system having a middle phase, and acidifying the middle phase so as to form the compound of Formula I.

2. The process according to claim 1 wherein said ether is selected from the group consisting of diethyl ether, methyl t-butyl ether and tetrahydrofuran.

3. The process according to claim 1 wherein said reduction with said hydrazine and said alkali metal hydroxide is in the presence of an aliphatic mono- or dialcohol.

4. The process according to claim 3 wherein said reduction with hydrazine and alkali metal hydroxide is carried out in the presence of diethylene glycol.

5. The process according to claim 1 wherein said product is treated first with said hydrazine and then with said alkali metal hydroxide so as to form said treated product.

6. The process according to claim 5 wherein said reduction with said alkali metal hydroxide is carried out at a temperature in a range from about 120 to 180° C.

7. The process according to claim 1 wherein said middle phase is treated with a mixture of water and a water-immiscible ether before acidifying said middle phase.

8. The process according to claim 1 wherein said compound of Formula I is separated from said middle phase by adding an aliphatic or cycloaliphatic hydrocarbon having a higher boiling point than the ether.

9. The process according to claim 1 wherein said ether is removed through distillation.

10. The process according to claim 1 wherein said compound of Formula III is prepared in a reaction by reacting 2-benzyl-4,4-dimethyl-1-pyrroline with an ω-halo-4-chloroacetophenone in a polar organic solvent in presence of an alkali metal hydrogencarbonate and an alkali metal carbonate in solid form.

11. The process according to claim 10 wherein said polar organic solvent in methanol.

12. The process according to claim 10 wherein said reaction is carried out in presence of solid sodium hydrogencarbonate.

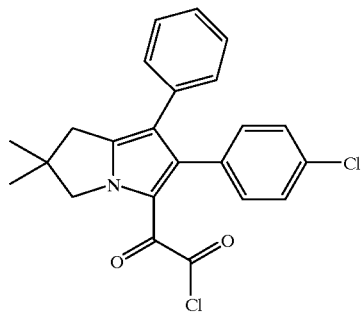

II

13. A compound comprising Formula I

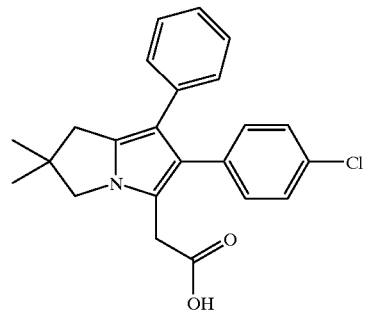

I wherein said compound is in crystalline form having a single endotherm in a DSC diagram, which is in a range of about 155° C. to 170° C.

14. The compound according to claim 13 wherein said compound has significant IR spectrum peaks of 1706; 1601; 1536; 1487; 1463; 1450; 1441; 1413; 1395; 1383; 1369; 1293; 1219; 1177; 1099; 1013; 836; 765 and 698.

15. The compound according to claim 12 having X-ray diffraction latice distance d values of 11.9; 4.2 and 4.0.

16. The compound according to claim 15 having the following d values: 11.9; 8.2; 7.9; 6.4; 5.9; 5.8; 5.6; 5.3; 5.0; 4.9; 4.7; 4.5; 4.4; 4.3; 4.2; 4.05; 4.0; 3.9; 3.7; 3.6; 3.55; 3.5; 3.4; 3.3; 3.25; 3.2; 3.1; 2.95; 2.9; 2.85; 2.8; 2.75; 2.7; 2.65; and 2.6.

17. A pharmaceutical composition comprising a compound as claimed in claims 13.

18. A process for the preparation of a compound of claim 13 comprising combining an ether solution of a compound of Formula I with an aliphatic or cycloaliphatic hydrocarbon having a boiling point higher than the ether of said solution, so as to obtain the compound of Formula I.

* * * * *